(12) United States Patent
LeBoeuf et al.

(10) Patent No.: US 7,872,752 B2
(45) Date of Patent: Jan. 18, 2011

(54) DETECTOR SYSTEM FOR UNIDENTIFIED SUBSTANCES

(75) Inventors: Steven Francis LeBoeuf, Raleigh, NC (US); Alexey Vasilievich Vert, Niskayuna, NY (US); Rui Chen, Clifton Park, NY (US); Radislav Alexandrovich Potyrailo, Niskayuna, NY (US)

(73) Assignee: Morpho Detection, Inc., Newark, CA (US)

(*) Notice: Subject to any disclaimer, the term of this patent is extended or adjusted under 35 U.S.C. 154(b) by 0 days.

(21) Appl. No.: 12/559,992

(22) Filed: Sep. 15, 2009

(65) Prior Publication Data

US 2010/0084573 A1 Apr. 8, 2010

Related U.S. Application Data

(63) Continuation of application No. 11/668,308, filed on Jan. 29, 2007, now Pat. No. 7,605,920.

(51) Int. Cl.
*G01N 21/64* (2006.01)
(52) U.S. Cl. ............... 356/417; 250/458.1; 250/461.1; 356/318
(58) Field of Classification Search ........... 356/317, 356/318, 417; 250/458.1, 459.1, 461.1, 461.2
See application file for complete search history.

(56) References Cited

U.S. PATENT DOCUMENTS

| 5,701,012 | A | 12/1997 | Ho |
| 5,801,828 | A | 9/1998 | Collins |
| 5,895,922 | A | 4/1999 | Ho |
| 6,166,804 | A | 12/2000 | Potyrailo et al. |
| 6,194,731 | B1 | 2/2001 | Jeys et al. |
| 6,541,264 | B1 | 4/2003 | Potyrailo |
| 7,279,688 | B2 * | 10/2007 | Campman ............ 250/461.1 |
| 7,304,741 | B2 | 12/2007 | Sadeghi et al. |
| 2004/0155202 | A1 | 8/2004 | Poteet et al. |
| 2007/0097366 | A1 | 5/2007 | LeBoeuf et al. |

* cited by examiner

*Primary Examiner*—F. L Evans
(74) *Attorney, Agent, or Firm*—Armstrong Teasdale LLP

(57) ABSTRACT

Disclosed herein is a detection system for identifying an unidentified substance in a sample, comprising light emitting sources, where at least one of the light emitting sources emits light in the infrared region; a circuit board; a trigger, that activates a pulse of electrons from the circuit board to the light emitting sources; a detector; and a central processing unit, where fluorescence generated from the unknown unidentified substance that is illuminated by light from the light emitting sources is collected in the detector and analyzed in the central processing unit.

19 Claims, 6 Drawing Sheets

DETECTOR SYSTEM FOR UNIDENTIFIED SUBSTANCES

CROSS-REFERENCE TO RELATED APPLICATION

The present invention is a continuation of and claims priority to U.S. patent application Ser. No. 11/668,308, filed Jan. 29, 2007.

BACKGROUND

This disclosure relates to a detection system for unidentified substances. In particular, this disclosure relates to a detection system for use in detecting the presence of proteins in a chemical spill or in a suspicious-looking stain.

When an unidentified or suspicious substance is first noticed (as the result of a spill), first responders (e.g., firefighters, police) are often called to the site. The first responders generally perform primary tests to try to identify whether the substance is a protein by performing a standard protein test. This test generally takes up to 5 minutes but uses reagents in order to make an identification. Since reagents are used to make the identification, the user has to have a degree of knowledge in the use of reagents. In addition, the user has to be able to identify and distinguish between reaction products of the reagents with the substance.

If the use of the reagent results in a positive detection of proteins, a HAZMAT (hazardous materials) team is called in to perform additional secondary tests. These tests provide additional details about the substance but are expensive and time-consuming. A significant portion of the time, hazardous proteins are never finally detected, thus resulting in a waste of time and resources. It is therefore desirable to have a protein detection system that can be easily transported to the site of a spill, is fast and accurate, and does not require the use of a specially trained individual to make an identification of the contents of the spill.

SUMMARY

Disclosed herein is a method of identifying a unidentified substance, comprising directing light from a light emitting source directly upon a stationary unidentified substance; collecting fluorescence from the unidentified substance in a detector; wherein the detector comprises a lock-in detection system; analyzing the fluorescence; and identifying the unidentified substance.

Disclosed herein is a detection system comprising a light emitting source; a circuit board; wherein the trigger is operative to trigger a pulse of electrons from the circuit board to the light emitting source; a detector; and a central processing unit, wherein fluorescence generated from an unknown unidentified substance that is illuminated by light from the light emitting source is collected in the detector and analyzed in the central processing unit.

DETAILED DESCRIPTION

The use of the terms "a" and "an" and "the" and similar references in the context of describing the invention (especially in the context of the following claims) are to be construed to cover both the singular and the plural, unless otherwise indicated herein or clearly contradicted by context. The modifier "about" used in connection with a quantity is inclusive of the stated value and has the meaning dictated by the context (e.g., it includes the degree of error associated with measurement of the particular quantity). All ranges disclosed herein are inclusive of the endpoints, and the endpoints are independently combinable with each other. The term "operative communication" between two units indicates that the two units communicate with one another. The operative communication can be of any kind such as for example, electrical communication, mechanical communication, thermal communication (e.g., convection), acoustic communication (e.g., ultrasound, or the like), electromagnetic communication (e.g., ultraviolet radiation, optical radiation, or the like), or the like, or a combination comprising at least one of the foregoing forms of communication. Electrical communication comprises the flow of electrons between two units, while mechanical communication involves the transfer of forces between two units via physical contact (e.g., via friction, adhesion, or the like) between the two units.

Disclosed herein is a detection system for the detection of unidentified substances. The detection system is hand-held and can be easily transported to the site of a spill, is fast and accurate and does not require the use of a specially trained individual to make an identification of the contents of the spill. The unidentified substances can be in powder or liquid form. In one embodiment, the detection system comprises a plurality of light emitting sources for generating light that is focused on the unidentified substances via a reflector. The reflector also acts as a light redirecting system for redirecting the light reflected by or generated from the unidentified substances. The detection system then analyzes the light reflected by or generated from the unidentified substances and provides the user with a spectral identification as well as the chemical identity of the unidentified substances. In one exemplary embodiment, the plurality of light emitting sources are LED's (light emitting diodes) that emit light in the ultraviolet, visible and infrared regions of the electromagnetic spectrum. In another exemplary embodiment, the detection system is a "point and click detection system" that can provide an identification of the unidentified substances at distances of up to 1 meter from the location of the unidentified substances.

As used herein, the term "unidentified substance" refers to any individual mass or collection of masses that can interact with energy, such as electromagnetic radiation, to produce signatures that can be collected and analyzed. The particles may be of varying scale. For example, the unidentified substance may be of an atomic scale or a molecular scale. At a larger scale, the unidentified substance may be a proteinaceous substance and may be a combination of molecules forming a spore, a virus, or a cell. For example, the unidentified substance may include a biological fluorophore. The unidentified substance can be considered to include organic as well as inorganic matter. The unidentified substance is generally stationary and does not exist in the form of a stream of particles that are mobile.

The categories of biological fluorophores include the aromatic amino acids, proteins, tryptophan, tyrosine, phenylalanine, nicotinamide adenine dinucleotide compounds, flavins, chlorophylls, or the like, or a combination comprising at least one of the foregoing biological fluorophores. In an exemplary embodiment, the biological fluorophores may include proteins. For example, the biological fluorophores may include tryptophan, riboflavin, bovine serum albumin, a nicotinamide adenine dinucleotide compound, or a combination comprising at least one of the foregoing biological fluorophores. Biological particles containing these fluorophores comprise biological spores, vegetative bacteria, proteins, DNA, viruses, toxins, and fragments of these particles.

In one embodiment, the disclosure relates to a method for the enhancement of the discrimination of unidentified substances by modulating one or more environmental parameters. In another embodiment, the fluorescence and/or phosphorescence signatures of the particles may be compared with the reference signatures. In an exemplary embodiment, a variation in the detectable response of the unidentified substances may be compared with a reference calibration curve to identify the unidentified substances. In certain embodiments, nicotinamide adenine dinucleotide hydrogen (NADH), indicative of biological activity or viability, may be coupled with information about fluorescence properties of other biological particles to detect the other unidentified substances.

Figure 1A:
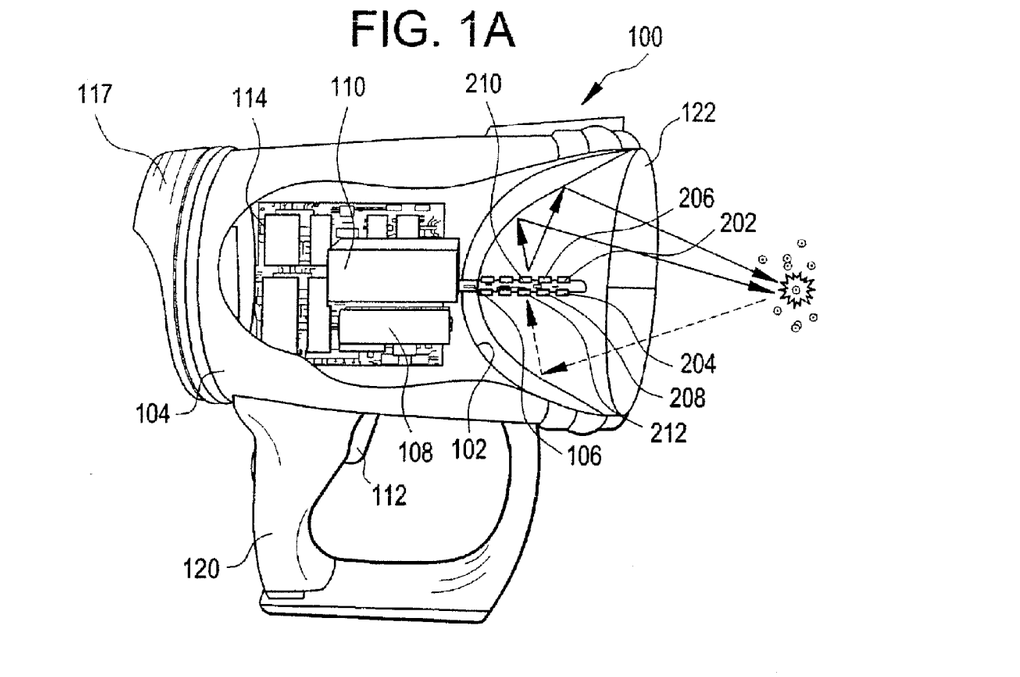
FIG. 1(a) is a side view of a hand-held detector constructed in accordance with an embodiment of the invention.
Figure 1B:
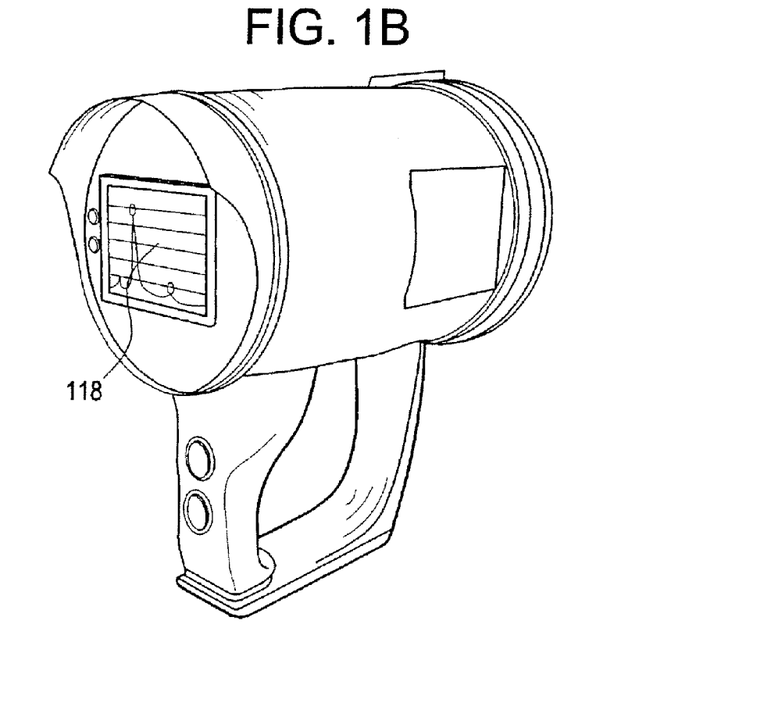
FIG. 1(b) is a perspective view of the front of the hand-held detector of FIG. 1(a)
Figure 1C:
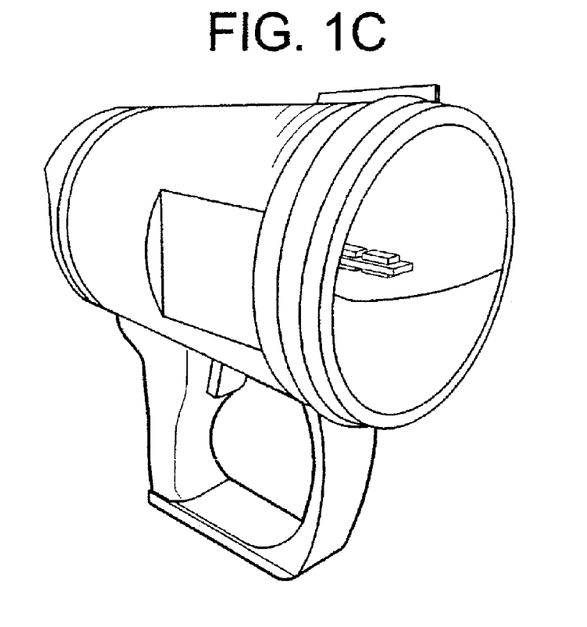
FIG. 1(c) is a perspective view of the back of the hand-held detector of FIG. 1(a)

With reference now to the FIGS. 1(a), 1(b) and 1(c), a detection system 100 comprises a single reflector 102 disposed in a case 104. The reflector 102 is disposed at the first end of the case 104. The second end of the case is opposed to the first end of the case and comprises an output device 118 upon which chemical identifications can be displayed. Disposed at the center of the reflector 102 is a circuit board 106 upon which are disposed a light emitting source 202 and a photodiode 204. The circuit board 106 is in operative communication with an electronic source 110 that supplies pulsed electrical charges that induce radiation in the light emitting source 202. The pulsing electronics 110 are in electrical communication with a source of power 108 and with a central processing unit (CPU) 114.

In one embodiment, the case 104 is a carrying case that comprises a first end and a second end that are opposingly disposed to one another. The case 104 can be manufactured from an organic polymer, a ceramic, or a metal. The case 104 can comprise a single piece or can comprise a plurality of pieces that are in mechanical communication with one another. As can be seen from the FIGS. 1(a), 1(b) and 1(c), the case 104 comprises a conduit that houses the reflector 102, the circuit board 106, the power source 108, and the pulsing electronics 110. The detection system 100 also includes a trigger 112. In an exemplary embodiment, the case 104 is provided with a handle 120 for transporting the detection system 100. As can be seen from the FIG. 1(a), the handle 120 is provided with a slot in which is disposed the trigger 112. The trigger 112 is used to activate the detection system 100. An alternate embodiment of a detection system is depicted in the FIG. 2. The detection system 100 includes a trigger comprising two buttons 113 for activating the detector and an alternative design for the handle 120.

The case 104 can have any cross-sectional shape that permits the user to conveniently transport it. The cross-sectional shape can be circular, square, rectangular, triangular, polygonal, or the like. An exemplary cross-sectional shape for the case 104 is a circular shape, which results in the case 104 being cylindrical in geometry.

The detection system 100 can have any desired dimensions. In an exemplary embodiment, it is desirable for the detector to be a hand-held detector. The detector can have a width (or diameter) of about 2 to about 12 inches, while the length can be about 3 to about 20 inches. As can be seen in the FIG. 1(a), an exemplary detector can be a hand-held detector, having a width (or diameter) of about 3 inches and a length of about 4 inches. Similarly, another exemplary hand-held detector may have a width of about 5 inches and a length of about 6 inches.

Figure 3:
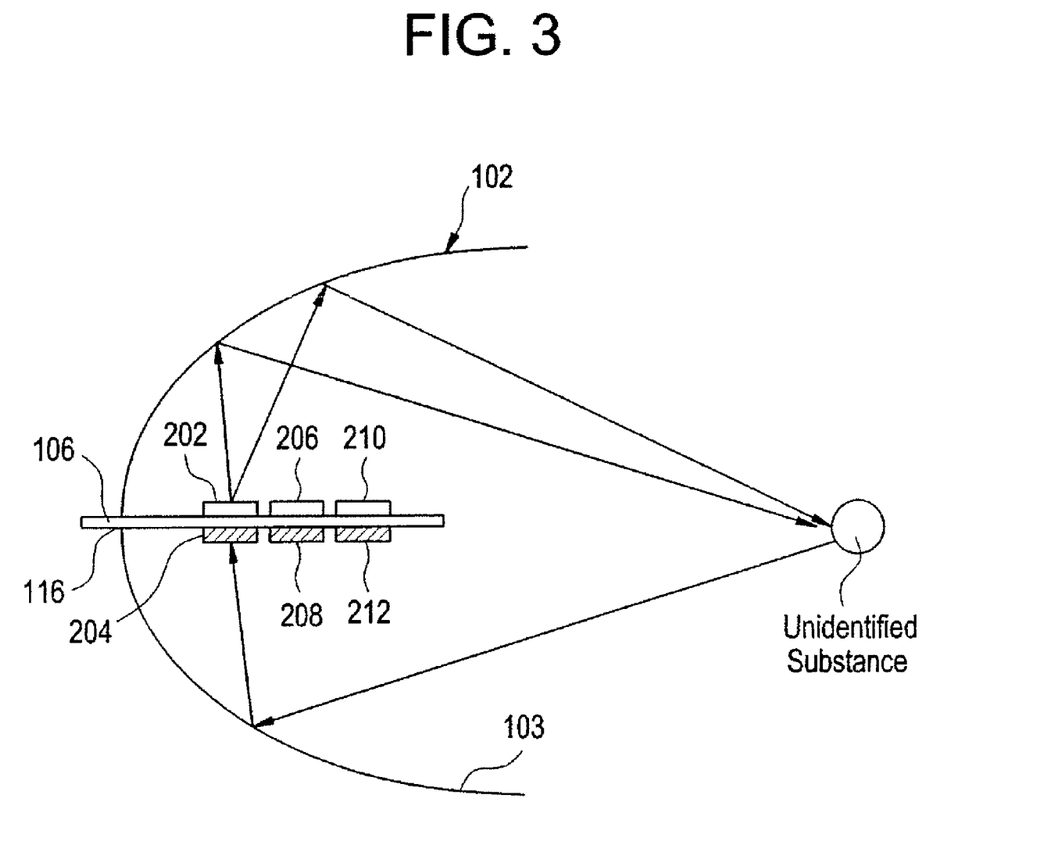
FIG. 3 illustrates one manner of functioning of the hand-held detector of FIG. 1(a) and FIG. 2.

With reference now to the FIG. 3, the reflector 102 comprises a highly polished inner reflective surface 103 that reflects light generated by the light emitting source 202 towards the unidentified substance. The reflector 102 can be parabolic, spherical, or elliptical in shape. An exemplary reflector 102 is elliptical in shape. The reflective surface 103 also reflects light reflected from the unidentified substance towards the detector 204. The reflective surface 103 also reflects light toward the detector 204 that is generated by the unidentified substance via a fluorescence process. The reflector 102 comprises a hole 116 at its center in which the circuit board 106 is disposed.

In one embodiment, the detector can comprise a single reflector. In another embodiment, the detector can comprise a plurality of reflectors. In yet another embodiment, the detector can comprise 2, 3, 4, 5, or more reflectors.

The reflector 102 generally has a focal point that permits identification of desired substances from a distance of about 1 millimeter up to about 1 meter, specifically about 5 millimeters to about 0.75 meter, more specifically about 1 centimeter to about 0.25 meter, and even more specifically about 10 centimeters to about 15 centimeters.

The circuit board 106 supports the light emitting source 202 and the detector 204. In other words, the light emitting source 202 and the detector 204 are disposed upon and are in intimate contact with the circuit board 106. The circuit board 106 transmits electricity generated in the pulsing electronics 110 to the light emitting source 202 and also transmits electricity generated in the detector 204 to the CPU 114 (FIG. 1(a)) for analysis. In an exemplary embodiment as depicted in the FIG. 3, the circuit board 106 can have disposed upon it a plurality of light emitting sources 202, 206, 210, or the like, or a plurality of photodetectors 204, 208, 212, or the like. In one embodiment, the light emitting sources 202, 206, 210, or the like, as well as the plurality of photodetectors 204, 208, 212, or the like, can be arranged on the printed circuit board 106 in a variety of different geometric arrangements. For example, in one embodiment, the light emitting sources 202, 206, 210, or the like, and the plurality of photodetectors 204, 208, 212, or the like, can be arranged linearly as shown in the FIG. 1(a). In another embodiment, the light emitting sources and/or the plurality of photodetectors can be arranged in a circular, random, periodic or aperiodic fashion as may be desired.

The circuit board 106 upon which the light emitting sources are disposed can be circuit board commercially available from the Bergquist Company with flip-chipped LEDs.

Figure 2:
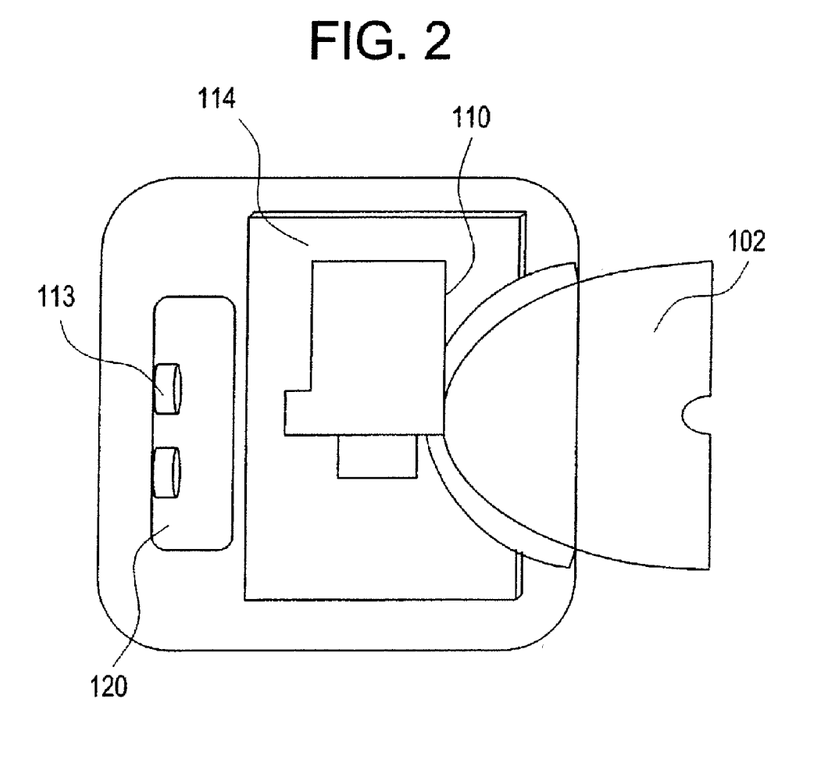
FIG. 2 is a side view of a hand-held detector constructed in accordance with an embodiment of the invention.

As can be seen in FIGS. 1-3, the circuit board 106 is disposed at the geometric center of the reflector 102 and passes through the hole at the geometric center of the reflector

102. In one embodiment, the circuit board 106 passes through the focal point of the reflector 102.

Figure 4:
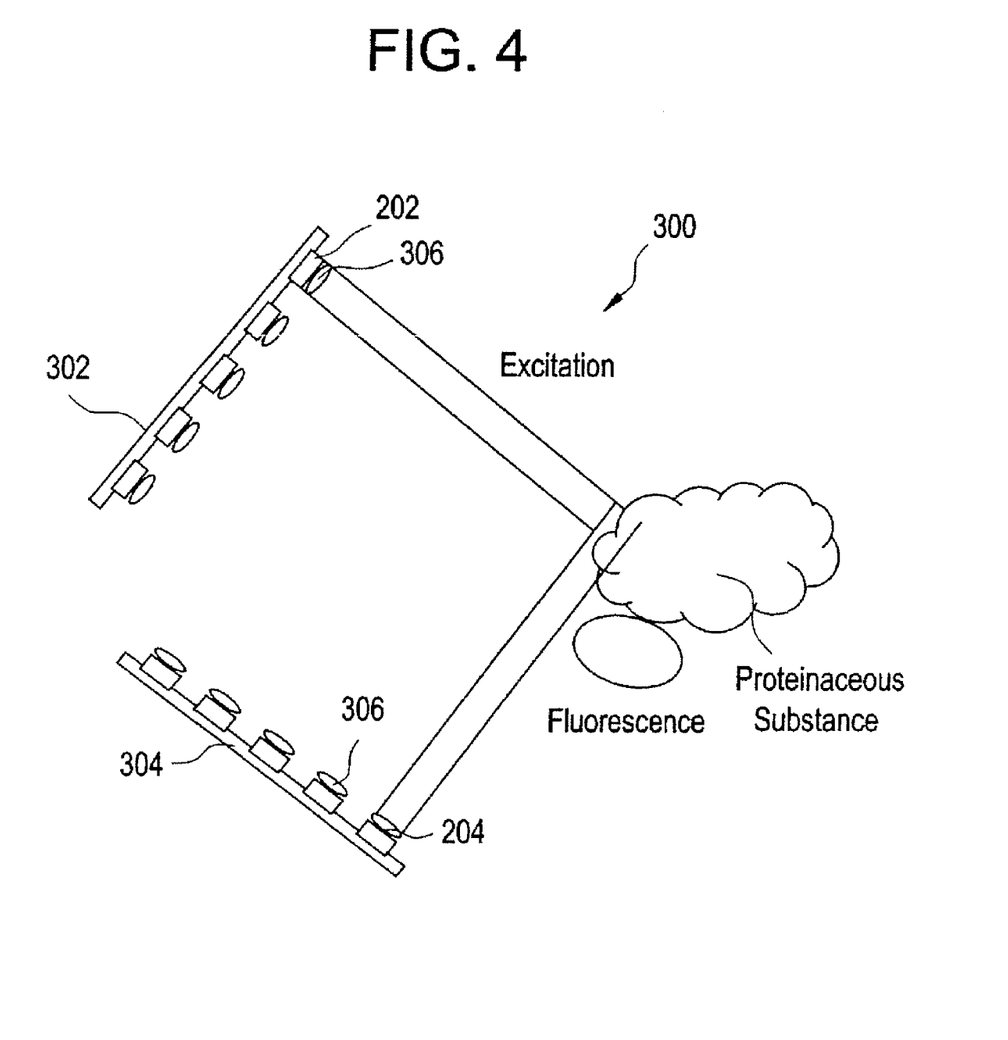
FIG. 4 illustrates another manner of functioning of the hand-held detector of FIG. 1(a) and FIG. 2.

FIG. 4 depicts another exemplary embodiment of the detection system 300 that does not employ a reflector. In this arrangement, a first circuit board 302 provides an electrical pulse (generated by pulsing electronics) to the light emitting source 202 to produce a first pulse of light. The light generated by the fluorescing of the unidentified substance is collected by the detector 204 and the electrical current generated in the detector 204 is transmitted to the CPU for analysis by a second circuit board 304. Each light emitting source 202 and each detector 204 has disposed upon it a lens 306 for collimating the excitation and for collecting the florescence. In this design, the elimination of the mirror renders the system more compact than the systems displayed in FIGS. 1 and 2. In addition, the light emitting sources 202 can be arranged to be circular. A circular pattern would provide an efficient spacing of the light emitting sources and the photodetectors.

It should be appreciated that any suitable light emitting source 202 may be utilized. It is desirable that the light emitting source 202 be capable of emitting a sufficiently high intensity light of the desired wavelength. By "sufficiently high intensity light" is meant a light of sufficient intensity to induce an effective optical signal, such as particle fluorescence. The term "wavelength" should be understood to encompass a range of wavelengths and to refer to a spectral range of electromagnetic energy. In an exemplary embodiment, the light emitting source 202 can include multi-wavelength ultraviolet (UV), visible and/or infrared (IR) electromagnetic radiation emitters. Infrared radiation emitters may be used for heating unidentified substances in order to activate fluorescence at different wavelengths from the samples. Furthermore, the light emitting source 202 may be pulsed to achieve the desired intensity of light without sacrificing reliability or lifetime. Another advantage of a very fast pulsed source, such as a light emitting diode (LED), would be to synchronize the detector to the source for the purpose of improving the signal to noise ratio. A heat sink may be attached to the light-emitting source 202 to enhance heat dissipation.

Examples of suitable light emitting sources 202 are light emitting diodes, including surface-emitting light emitting diodes, ultraviolet light emitting diodes, edge-emitting light emitting diodes, resonant cavity light emitting diodes, broad band light emitting diodes, flip-chipped light emitting diodes, gas-discharge lamps, mercury lamps, filament lamps, blackbody radiators, chemo-luminescent media, organic light emitting diodes, phosphor upconverted sources, plasma sources, solar radiation, sparking devices, vertical light emitting diodes, wavelength-specific light emitting diodes, lasers, laser diodes, or the like, or a combination comprising at least one of the foregoing light emitting sources. Exemplary light emitting sources are UV-visible light emitting sources 202.

Examples of suitable LEDs that are used for the emission of light are aluminum gallium arsenide (AlGaAs)—red and infrared color; aluminum gallium phosphide (AlGaP)—green color; aluminum gallium indium phosphide (AlGaInP)—high-brightness orange-red, orange, yellow, and green colors; gallium arsenide phosphide (GaAsP)—red, orange-red, orange, and yellow colors; gallium phosphide (GaP)—red, yellow and green colors; gallium nitride (GaN)—green, pure green (or emerald green) colors, and blue also white (if it has an AlGaN or InAlGaN quantum well); indium gallium nitride (InGaN)—near ultraviolet, bluish-green and blue colors; silicon carbide (SiC) as substrate—blue color; silicon (Si) as substrate—blue color; sapphire ($Al_2O_3$) as substrate—blue color; zinc selenide (ZnSe)—blue color; diamond (C)—ultraviolet color; aluminum nitride (AlN); aluminum gallium nitride (AlGaN)—near to far ultraviolet, or a combination comprising at least one of the foregoing LEDs. In one embodiment, packaged LEDs comprising their own optics, such as, for example, ball shaped lenses, may be used.

The light emitting source 202 generally emits radiation having a wavelength that promotes fluorescence in the unidentified substances. The light emitting source 202 may emit radiation having a wavelength of about 100 nanometers (nm) to about 1,000 nm. An exemplary wavelength for the light emitting source 202 is about 200 to about 450 nm.

The light emitting source 202 generally can be activated to emit electromagnetic radiation upon the application of a voltage of about 1 to about 20 volts. An exemplary voltage is about 4 to about 9 volts.

An optional optically transparent window 122 (FIG. 1(*a*)) may be located at the end of the case 104 opposing the end including the output device 118. The optically transparent window 122 encloses the circuit board 106 and may include an optical filter for lessening the amount of parasitic light that is in the range of the detection spectrum from impinging upon the reflector 102 and producing parasitic signals in the form of scattered light.

The detector 204 can be a photodetector that can capture a single photon or a collection of single photons. Examples of suitable photodetectors are photoconductors, photodiodes, photomultiplier tubes, an avalanche photodiodes, any photodetector capable of detecting single photons or collections of single photons, or a combination comprising at least one of the foregoing photodetectors. The detector 204 may also comprise charge coupled device (CCD) imagers, spectral imagers, or a combination comprising at least one of the foregoing detectors. An exemplary photodetector is a filtered photodiode commercially available from Hamamatsu. As noted above, both the light emitting source 202 and the detector 204 can optionally have disposed upon them a lens that collimates the excitation from the light emitting source as well as for collecting the florescence from the unidentified substances.

The pulsing electronics 110 supply a voltage to the light emitting source 202 via the circuit board 106. The application of the appropriate voltage to the light emitting source 202 promotes the light emitting source to emit light in the UV, visible and infrared regions of the electromagnetic spectrum. The pulsing electronics 110 are generally activated upon the depression of the trigger 112. Upon depressing the trigger 112, a power source 108 supplies power to the pulsing electronics 110. The power source 108 is generally a commercially available battery that is capable of supplying a voltage of about 12 volts. The pulsing electronics 110 supplies power to the light emitting sources 102 to emit light as detailed above.

In an exemplary embodiment, the pulsing electronics 110 generally supply the requisite voltage that activates the light emitting sources. These voltages are indicated above. The pulsing electronics 110 supply the aforementioned voltages to the light emitting sources at currents of about 1 to about 400 milliamperes (mA). An exemplary amount of current used to activate the light emitting sources is about 20 to about 100 mA. The pulsing electronics 110 pulse the light emitting sources at a frequency of about 10 to about 10,000,000 hertz (Hz). In an exemplary embodiment, the pulsing electronics 110 pulse the light emitting sources at a frequency of about 10,000 to about 100,000 Hz. The pulsing electronics 110 can be commercially purchased from Supertex. The pulsing of the light emitted from the light emitting source 202 facilitates a reduction in the background noise thereby improving signal resolution and consequently sample identification.

The CPU 114 generally functions to process electrical signals generated in the detector 204 and converts these signals into a spectrum that indicates the identity of the unidentified substance. The CPU 114 generally comprises an analysis system (not shown) that receives signals from the detector 204 and conveys the signals to the output device 118. The analysis system may be a univariate analysis system, or a multivariate analysis system.

Where the optical spectrum comprises several wavelengths or an entire spectrum over a certain range, the optical characteristics of the unidentified substance may be determined using multivariate calibration algorithms such as Partial Least Squares Regression (PLS), Principal Components Regression (PCR), and the like.

Given a large enough span of calibration samples, multivariate calibration models are generally more robust than univariate models due to enhanced outlier detection capabilities and increased tolerance toward slight shifting in peak position or band shape. In addition, multivariate calibration models allow for measurement of more than one variable or component of interest from the unidentified substance. PLS models correlate the sources of variation in the spectral data with sources of variation in the sample. Preferably, the PLS model is validated by statistical techniques.

Examples of statistical techniques are leave one out cross-validation, Venetian blinds, random subsets, or a combination comprising at least one of the foregoing statistical techniques. All or part of the steps in the analysis of response of optical signals from the particle stream may be coded or otherwise written in computer software, in a variety of computer languages including, but not limited to, C, C++, Pascal, Fortran, Visual Basic®, Microsoft Excel, MATLAB®, Mathematica®, Java, or the like. Results may be illustrated using known pattern recognition tools.

The output device 118 may include a display (e.g., a screen) or printer, to output the signatures generated during the identification of the unidentified substances. In an exemplary embodiment, the second end of the case 104 may comprise a cover 117 that further comprises an output device 118. An exemplary output device is a screen that can be used to produce a spectrum of the fluorescence generated by the unidentified substance. The screen can also identify the unidentified substance by name or Chemical Abstract number.

As noted above, the detection system comprises a point and click detection system. In an exemplary embodiment, in one manner of proceeding, the hand-held detection system 100 is pointed at a suspicious substance on a surface such as the floor. Upon activating the trigger 112, a pulse of electricity is generated in the pulsing electronics 110. The pulse of electricity travels to the circuit board activates the light emitting source 202 which emits light of a particular desired frequency. The light is reflected by the reflector 102 and impinges upon the suspicious substance. Fluorescence from the suspicious substance is collected by the detector 204 and transmitted.

In one exemplary embodiment, the light emitting source 202 and the detector 204 may be tuned to the absorption and emission profiles of various particles. For example, a first light emitting source 202, may emit light at a first wavelength at which a predetermined particle fluoresces while a second light emitting source 206 may emit light at a second wavelength at which a second predetermined particle fluoresces. It should be appreciated that certain particles fluoresce at more than one wavelength, and thus the first and second predetermined particles indeed may be the same particles. Alternatively, each of the light emitting sources 202, 206, 210 may emit light at a wavelength at which several types of particles fluoresce and each of the detectors 204, 208, 212 are tuned to detect the fluorescent light at wavelengths differing from the other of the detectors 204, 208, 212.

When several excitation wavelengths are employed and corresponding emission spectra are collected, this collection of spectra constitutes an excitation-emission map. Suitable methods for determination of fluorescence-excitation maps are provided in, for example, U.S. Pat. Nos. 6,166,804 (Potyrailo et al.) and 6,541,264 (Potyrailo et al.). Fluorescence excitation-emission maps are useful because they provide a more comprehensive spectral signature for a single species and provide a more detailed capability to reveal if more than one fluorescent species are present in a measured sample.

For example, a 280 nm ultraviolet (UV) source and a 365 nm UV source can be turned on alternatively such that a unidentified substance is hit with one UV wavelength at a time. Bacteria will fluoresce primarily in the 340 nm range, due to protein fluorescence, upon exposure to 280 nm UV radiation. Bacteria will also fluoresce primarily in the 430 to 550 nm range upon excitation with 365 nm UV light, due to NADH and flavin fluorescence. In contrast, many common fluorescent interferents, such as diesel soot and many vegetable oil aerosols, show significant fluorescence at only one of these excitation wavelengths. Thus, with one photo detector optically filtered at 340 nm and another photo detector optically filtered at 430-550 nm, a sufficient algorithm can be developed for discriminating airborne bacteria from common interferents. Table 1 provides a summary of fluorescence ranges for bio-agents and common interferents exposed to light at various wavelengths.

TABLE 1

| Agent | $\lambda_{excit}$ = 280 nm | $\lambda_{excit}$ = 340/365 nm | $\lambda_{excit}$ = 405 nm |
|---|---|---|---|
| Vegetative Bacteria | Tryptophan (320-360 nm); Flavins (500-600 nm) | NADH + Flavins (430-600 nm) | Flavins (500-600 nm) |
| Spores | Tryptophan & Flavins | Possible NADH, but dim | Flavins (500-600 nm) |
| Viruses | Tryptophan & Flavins | Non-detectable | Non-detectable |
| Toxins | Tryptophan | Non-detectable | Non-detectable |
| Vegetable Oil | Non-detectable | 400-550 nm | 450-500 nm |
| Diesel Soot | Dim 380-500 nm | Dim 380-500 nm | 410-650 nm |
| Fluospheres | Dim 280 nm | 400-500 nm | Non-detectable |
| Road Dust | Non-detectable | Non-detectable | Non-detectable |

Figure 5:
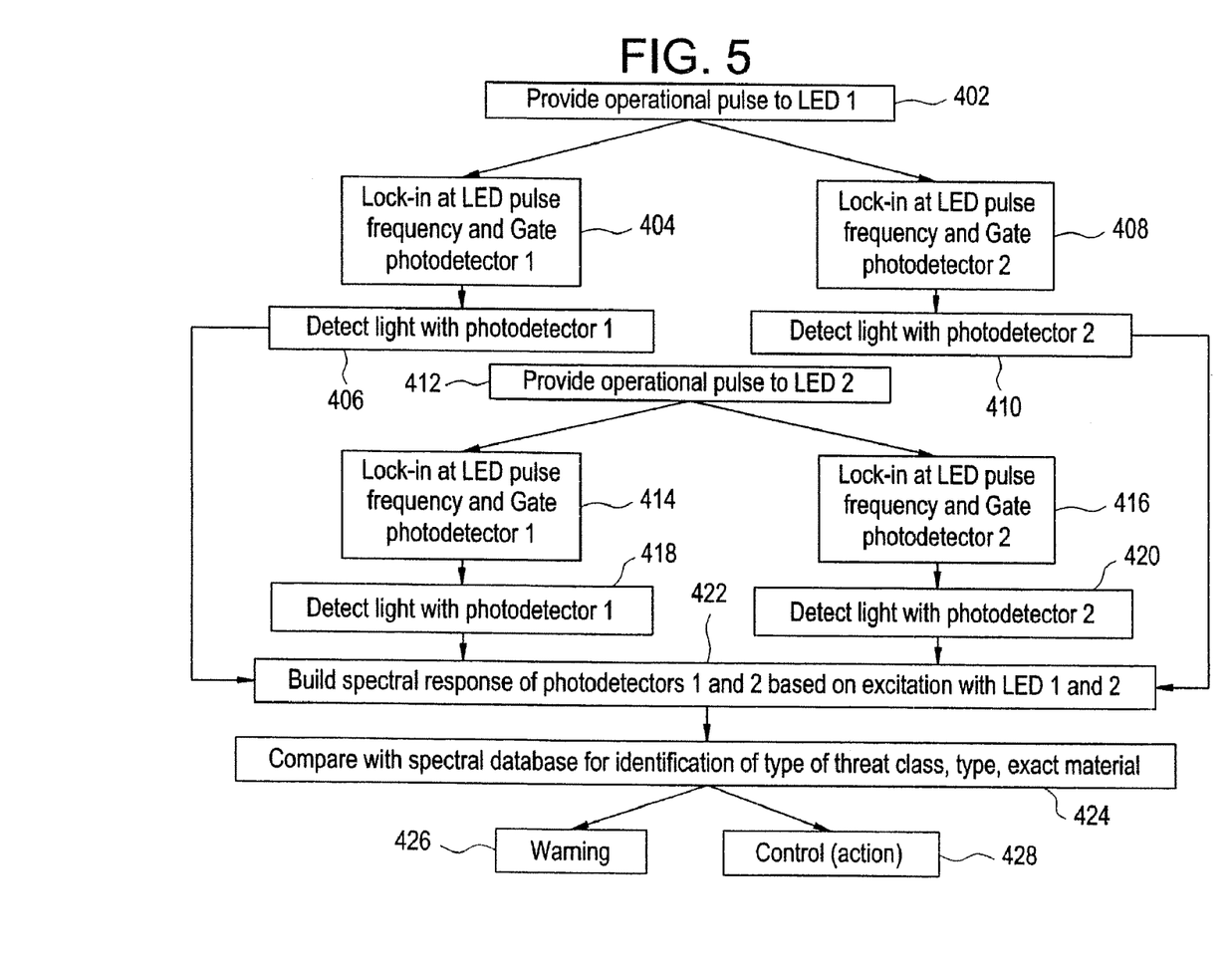
FIG. 5 illustrates a flow diagram exemplifying a process for using a plurality of LEDs and a plurality of optical filter/photodetector pairs to detect an unidentified substance in accordance with an embodiment of the invention.

In another embodiment, depicted in the schematic flow chart in the FIG. 5, a plurality of LEDs and a plurality of optical filter/photodetector pairs may be used to detect an unidentified substance. In the FIG. 5, in the steps 402, 404, 406, 408, 410, 422 and 424, a first light emitting source 202 (e.g., a LED) is pulsed and a first detector 204 and/or a second photodetector 208 (e.g., a photodiode) is arranged to detect the light arriving at this first detector over the period of operation of the first light emitting source 202 in addition to a small delay (e.g., in nanoseconds) associated with a fluorescence process from the sample.

Often, there are situations when measurements of analytical signal from the powder sample are performed in presence of unwanted optical interference. A non-limiting example of unwanted optical interference is ambient light. Several methods that are applicable to the rejection of unwanted optical radiation from interfering with measurements of an analytical signal include lock-in detection, temporal gating, polarization gating, phase resolved optical detection, Fourier transform filtering, or the like, or a combination comprising at least one of the foregoing.

In one embodiment, the detector is gated to detect light associated with a fluorescence process from the sample. In another embodiment, the detector is a photodetector with an optical filter that selectively permits the detection of light having a specific wavelength.

In yet another embodiment, the arrival of light (associated with a fluorescence process from the sample) is detected by the use of a lock-in detection technique. Lock-in detection is a technique to recover a signal even in the presence of broad band noise whose magnitude is several times greater than the signal itself. When lock-in detection is used, the photodetector is locked into frequency of the light source, not just gated, this allows a virtually blind response to the ambient light and a very high signal to noise ratio. In lock-in detection, a light from the light emitting source is pulsed and a photodetector is locked to a frequency of the pulse and operates to detect light with a selected time gate width. In another embodiment, a light from the light emitting source is pulsed and a signal to the photodetector is amplified with a lock-in amplifier at the frequency at which the light from the light emitting source is pulsed.

As a result, all sources can be pulsed simultaneously at different frequencies. This approach provides a lock-in detection of light detected with the photodetector only after pulsing of an LED and significantly reduces or eliminates effects of ambient light on the device performance. The effects of ambient light that provide elevated background signals are therefore minimized. Without gating of the photodetector after LED pulsing, these background signals are too high to detect weak fluorescence signals from a sample.

A second light emitting source 206 is then pulsed and a second detector 208 is gated (in steps 412, 414, 416, 418, 420, 422 and 424) to detect the light arriving at the second detector 208 over the time of operation of the second light emitting source 206 plus a small delay (in nanoseconds) associated with a fluorescence process from the sample. In this embodiment, the first light emitting source 202 and the second light emitting source 206 are emitting at different wavelengths and the first detector 204 and the second detector 208 are detecting light at different emission wavelength regions.

In yet another exemplary embodiment not depicted in the FIG. 5, the first light emitting source 202 and the second light emitting source 206 are emitting at different wavelengths and only one detector 204 is used that detects light in a broad wavelength region, of about 200 to about 1000 nm, more specifically about 220 nm to about 900 nm, and even more specifically about 230 nm to about 850 nm.

Figure 6:
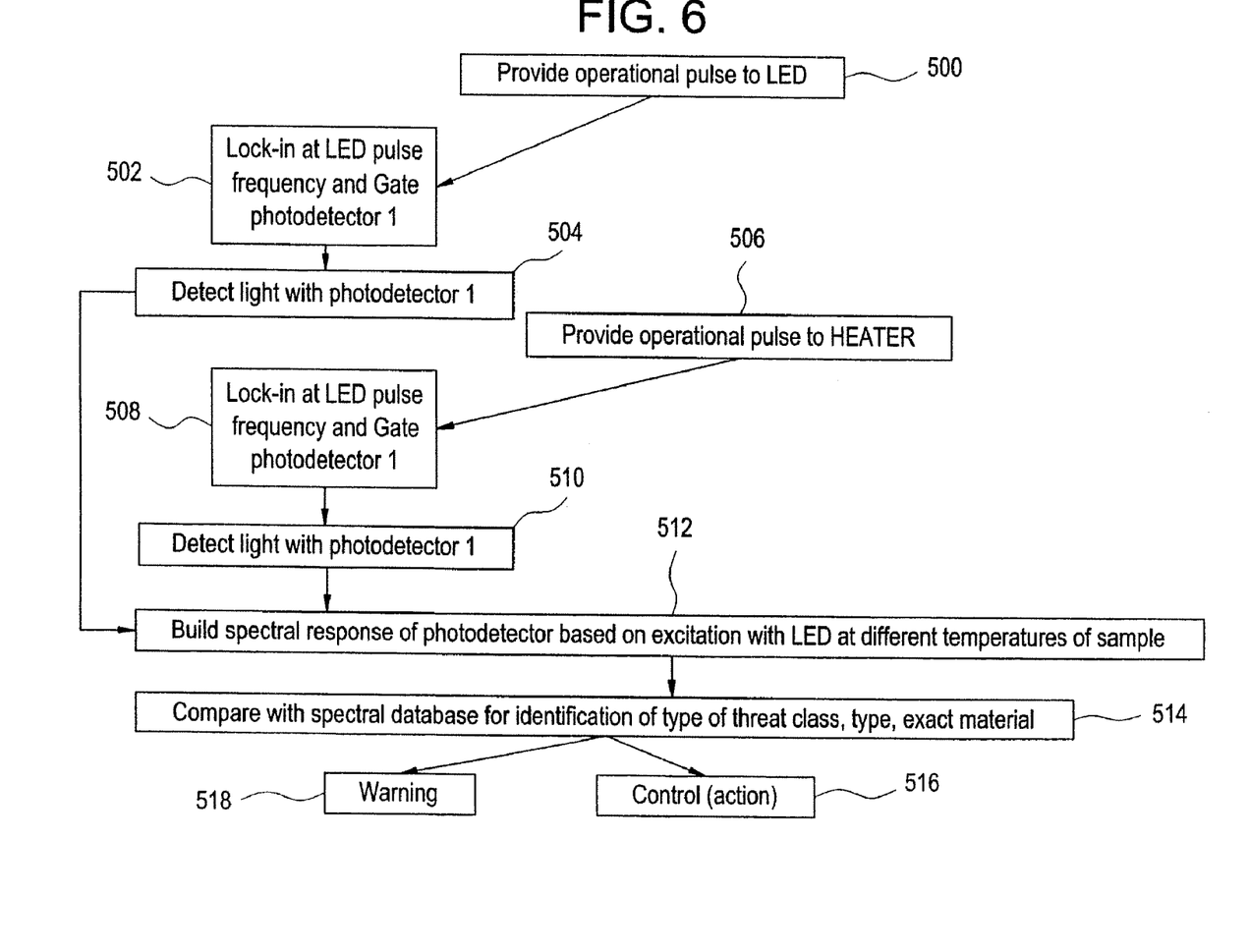
FIG. 6 illustrates a flow diagram exemplifying a process for using a plurality of LEDs and a plurality of optical filter/photodetector pairs to detect an unidentified substance in accordance with an embodiment of the invention.

In yet another embodiment depicted in steps 500-504 in the schematic flow diagram of FIG. 6, in addition to using the first light emitting source 202 and the detector 204 for fluorescence detection, a second light emitting source 204 (step 506) (denoted as "heater" in FIG. 6) is used to heat the unidentified sample. This second light emitting source 204 can be an infrared LED source, or a infrared laser diode. This second light emitting source 204 serves as a heater, to heat the unidentified sample locally. Heating the sample can give rise to fluorescence at different wavelengths, which can be used to improve detection capabilities (steps 508-514).

In summary, the detection system 100 can be used in a variety of ways to identify unknown unidentified substances. In one embodiment, a plurality of light emitting sources can be used in conjunction with a single detector. In another embodiment, a single light emitting source can be used in conjunction with a plurality of detectors. In yet another embodiment, a plurality of light emitting sources can be used in conjunction with a plurality of detectors. In yet another embodiment, a plurality of light emitting sources can be pulsed sequentially or simultaneously while a single detector or a plurality of detectors can be gated to detect the fluorescence generated by the unidentified substance. The gating of the detectors can be programmed to occur simultaneously or sequentially.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A detection system for identifying an unidentified substance in a sample, comprising:
   a plurality of light emitting sources, wherein at least one of the plurality of light emitting sources emits light in an infrared region for heating the unidentified substance;
   a circuit board;
   a trigger, wherein the trigger is operative to trigger a pulse of electrons from the circuit board to the plurality of light emitting sources;
   a detector comprising a photodetector for collecting fluorescence generated from the unidentified substance; and
   a central processing unit, wherein the fluorescence generated from the unidentified substance that is illuminated by light emitted from the plurality of light emitting sources is collected in the detector and analyzed in the central processing unit to identify the unidentified substance in the sample.

2. The detection system of claim 1, wherein the trigger is further operative to promote a pulse of electricity from a battery to the circuit board.

3. The detection system of claim 1, wherein one of the plurality of light emitting sources is a light emitting diode.

4. The detection system of claim 3, wherein the light emitting diode is a surface-emitting light emitting diode, broad band light emitting diode, ultraviolet light emitting diode, edge-emitting light emitting diode, resonant cavity light emitting diode, flip-chipped light emitting diode, organic light emitting diode, vertical light emitting diode, wavelength-specific light emitting diode, laser light emitting diode, or a combination comprising at least one of the foregoing light emitting diodes.

5. The detection system of claim 1, wherein one of the plurality of light emitting sources is an infrared light emitting diode that is used to heat the unidentified substance.

6. The detection system of claim 1, wherein the unidentified substance is not in the form of a stream of particles.

7. The detection system of claim 1, wherein the light from one of the plurality of light emitting sources has a wavelength of about 200 to about 450 nanometers.

8. The detection system of claim 1, wherein the detector is a photoconductor, a photodiode, a photomultiplier tube, an avalanche photodiode, or a combination comprising at least one of the foregoing photodetectors.

9. The detection system of claim 1, wherein the central processing unit uses a univariate analysis system, a multivariate analysis system, or a combination comprising at least one of the foregoing systems.

10. The detection system of claim 1, wherein the plurality of light emitting sources is an array of light emitting diodes.

11. The detection system of claim 1, wherein the plurality of light emitting sources is an array of light emitting sources and wherein a first light emitting source of the plurality of light emitting sources excites fluorescence from the unidentified substance and the at least one of the plurality of light emitting sources emitting light in an infrared region heats the unidentified substance.

12. The detection system of claim 1, wherein the light from the plurality of light emitting sources is pulsed and the photodetector is locked to this pulse frequency.

13. The detection system of claim 1, wherein a light from the plurality of light emitting sources is pulsed and a photodetector is locked to a frequency of the pulse and operates to detect light with a selected time gate width.

14. The detection system of claim 1, wherein a light from the plurality of light emitting sources is pulsed and a signal from the photodetector is detected with a lock-in amplifier at the frequency at which the light from the plurality of light emitting sources is pulsed.

15. The detection system of claim 1, wherein the sample is one of a powder and a liquid.

16. The detection system of claim 1, wherein the light emitting source that emits light in the infrared region is configured to promote fluorescence from the unidentified substance.

17. The detection system of claim 1, wherein one of the plurality of light emitting sources emits lights in an ultraviolet region.

18. The detection system of claim 1, wherein one of the plurality of light emitting sources emits lights in a visible region.

19. The detection system of claim 1, wherein the unidentified substance comprises one of organic matter, inorganic matter, and a biological fluorophore.

* * * * *